United States Patent [19]

Sakagami et al.

[11] Patent Number: 4,791,197
[45] Date of Patent: Dec. 13, 1988

[54] CEPHALOSPORIN COMPOUNDS

[76] Inventors: Kenji Sakagami, 156, Furukawa-cho, Saiwai-ku, Kawasaki-shi, Kanagawa-ken; Kunio Atsumi, 3-16-11, Hiyoshi, Kohhoku-ku, Yokohama-shi, Kanagawa-ken; Ken Nishihata, 23-3, Shiratoridai, Midori-ku, Yokohama-shi, Kanagawa-ken; Takashi Yoshida, 2-9-22, Himonya, Meguro-ku, Tokyo; Shunzo Fukatsu, 1-13, Ichigaya Tamachi, Shinjuku-ku, Tokyo, all of Japan

[21] Appl. No.: 751,208
[22] Filed: Jul. 2, 1985
[30] Foreign Application Priority Data
   Jul. 9, 1984 [JP] Japan ............... 59-140722
[51] Int. Cl.$^4$ .............. C07D 501/22; A61K 31/545
[52] U.S. Cl. ........................... 540/227; 540/225
[58] Field of Search ............... 540/224, 227; 514/203, 514/206

[56] References Cited

U.S. PATENT DOCUMENTS

| 4,416,880 | 11/1983 | Bobeg et al. | 514/206 |
| 4,500,716 | 2/1985 | Kinast | 540/228 |
| 4,634,697 | 1/1987 | Hamashima | 540/227 |

FOREIGN PATENT DOCUMENTS 93982 11/1982 Japan.
105993 6/1983 Japan.
93086 5/1984 Japan.
34957 2/1985 Japan.

OTHER PUBLICATIONS

Cephalosporins and Penicillins, Chemistry & Biology, Chapter 11, Edited by E. H. Flynn, Academic Press, 1972, N.Y., N.Y.

Primary Examiner—Nicholas S. Rizzo
Attorney, Agent, or Firm—Larson and Taylor

[57] ABSTRACT

A new cephalosporin compound is now provided, which is useful as antibacterial agent and is represented by the general formula (I)

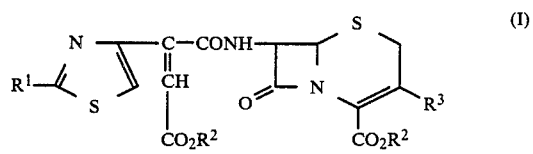

wherein $R^1$ is an amino group or a protected amino group; $R^2$ is a hydrogen atom, a salt-forming cation or a carboxyl-protecting group; $R^3$ is a hydrogen atom, a halogen atom, a lower alkylthio group, a lower alkoxyl group, a vinyl group or a group of the formula: —$CH_2Y$ where Y is a hydrogen atom, a halogen atom, an acyloxy group, an unsubstituted or substituted heterocyclic thio group or an unsubstituted or substituted pyridinio group, and a pharmaceutically acceptable salt or ester thereof.

1 Claim, No Drawings

CEPHALOSPORIN COMPOUNDS

SUMMARY OF THE INVENTION

This invention relates to a new cephalosporin compound and pharmaceutically acceptable salt or ester thereof which are useful as antibacterial agent. More particularly, this invention relates to a new cephalosporin compound which bears an α-(substituted methylene)-α-aminothiazolylacetyl group as the side chain at the 7-position of the cephem nucleus. This invention also relates to a pharmaceutical composition comprising the new cephalosporin compounds as active ingredient.

BACKGROUND OF THE INVENTION

We, present inventors, have disclosed in Japanese patent application No. 142558/83 (published as Japanese patent application first publication "Kokai" No. 34957/85 laid open on 22nd Feb. 1985) that an acyl group similar to the α-(substituted methylene)-α-aminothizolyl-acetic acid residue or more particularly, the 2-(substituted methylene)-2-(2-aminothiazol-4-yl)-acetic acid residue, presented as the side chain at the 7-position of the new cephalosporin compounds according to this invention is useful as agent for chemical modifications of penicillins and cephalosporins. Also, some β-lactam-compounds which are closely related to the new cephalosporin compounds according to this invention are disclosed in Japanese patent application first publication "Kokai" No. 93982/82, No. 105993/83 and No. 93086/84. The known cephalosporin compounds as disclosed in these three Japanese patent application first publications also have an α-(substituted methylene)-α-aminothiazolyl-acetic acid residue as the 7-acyl side chain, similarly to the cephalosporin compounds according to this invention. The new cephalosporin compounds of this invention are different from the above-mentioned known cephalosporin compounds in the respect of the kind of the substituent born on the α-methylene group of the α-(substituted methylene)-α-aminothiazolylacetyl group at the 7-position of the cephalosporin structure.

Cephalosporin-series antibiotics are known to be highly and broadly active against a variety of gram-positive and gram-negative bacteria. Various kinds of semi-synthesized cephalosporin compounds have already been available commercially and applied clinically for the therapeutic treatment of various infections diseases. But, only a very few ones amongst these semi-synthesized cephalosporin compounds are practically effective against the strains of bacteria of the genus Pseudomonas and Proteus. These known cepahlosporin compounds are also degradable by a β-lactamase which is produced by some resistant strains of bacteria, and they exhibit only a poor activity against some resistant strains of bacteria which have now been a target of clinical treatments of bacterial infections (see: W. E. Wick "Cephalosporins and Penicillins, Chemistry and Biology", E. H. Flynn, Academic Press, New York, N.Y., 1972 Chapter 11.)

We, the present inventors, have now succeeded in preparing as the new compound, cephalosporin compounds represented by the general formula (I) as shown below, and we have found that said new cephalosporin compounds exhibit a very wide range of antibacterial spectrum that these compound are highly active not only against a variety of gram-positive and gram-negative bacteria but also against some of resistant strains of bacteria. We have thus reached this invention.

DETAILED DESCRIPTION OF THE INVENTION

According to a first aspect of this invention, there is provided a new cephalosporin compound of the general formula (I)

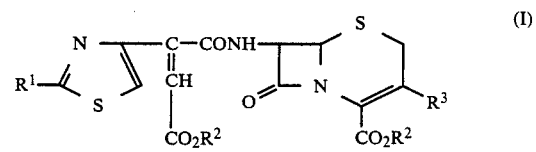

wherein $R^1$ is an amino group or a protected amino group; $R^2$ is a hydrogen atom, a salt-forming cation or a carboxyl-protecting group; $R^3$ is a hydrogen atom, a halogen atom, a lower alkylthio group, a lower alkoxyl group, a vinyl group or a group of the formula: $-CH_2Y$ where Y is a hydrogen atom, a halogen atom, an acyloxy group, an unsubstituted or substituted heterocyclic-thio group or an unsubstituted or substituted pyridinio group, and a pharmaceutically acceptable salt or ester thereof.

The cephalosporin compound according to this invention includes two isomers (E) and (Z), depending on the configuration of the substituent born on α-methylene group of the 7-acyl side chain. The cephalosporin compound of this invention, therefore, covers the (E)-isomer, the (Z)-isomer and the mixture thereof. The (Z)-isomer of the cehalosporin compound according to this invention is of such a form in which the group $-CO_2R^2$ (carboxyl or carboxylate group) and the amido moiety take "cis"-configuration around the double bond (of the methylene group) as shown in the general formula (I). The (E)-isomer of the cepahlosporin compound is of such form in which the group $-CO_2R^2$ and the amido moiety take "trans"-configuration around and double bond (of the methylene group).

Some of the terms used in the specification have the meanings as defined below:

The term "lower" means that a group concerned is containing 1 to 6 carbon atoms, unless otherwise stated. The amino-protecting group includes a conventional amino-protecting group which may easily be removed by acid hydrolysis, for example, an alkoxycarbonyl group such as tert.-butoxy-carbonyl group; an acyl group such as a formul group and a chloroacetyl group; and a trityl group.

The salt-forming cation which $R^2$ represents is a conventional metal cation and may include cation of an alkali metal, an alkaline earth metal and ammonium. The carboxyl-protecting group which $R^2$ represents is a carboxyl-protecting group conventionally used for cephalosporins and may include an aryl group, a lower alkyl group, a lower alkoxymethyl group, a lower alkylthio methyl group and a lower alkanoyloxymethyl group and the like. The group $R^2$ may also include a metabolically unstable group which is easily hydrolyzed and cleaved in vivo and which may include, for example, a lower alkoxycarbonyloxyalkyl group, a lower alkylcarbonyloxyalkyl group, an unsubstituted or substituted (2-oxo-1,3-dioxolene-4-yl) methyl group and the like.

The term "halogen" means a chlorine, a bromine and an iodine atom, and it is preferably a chlorine or bromine atom. A chlorine atom is most preferred.

"Acyloxy group" which Y in the group —CH₂Y represents includes, for example, a lower alkanoyloxy group, particularly an acetoxy group; a lower alkoxycarbonyl group such as a methoxycarbonyl; an acyl group derived from carbamic acid which may be N-substituted, such as a carbamoyloxy group and a N-methylcarbamoyloxy group.

"Unsubstituted or substituted heterocyclic thio" group which Y of the group —CH₂Y stands for may include a pyridiniothio group represented by the formula (II)

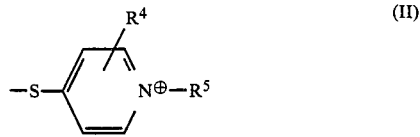

wherein R⁴ and R⁵ are the same or different and each are a hydrogen atom or an unsubstituted or substituted lower alkyl group; or an unsubstituted or substituted heterocyclic group which contains 1 to 4 nitrogen atoms in the ring together with or without further hetero atom as selected from oxygen and sulfur atom, and to which a thio group is attached at one ring carbon atom present in the heterocyclic group. Particular examples of such heterocyclic group just above include an aromatic cyclic group or a partially saturated five- or six-membered monocyclic group such as diaza-, triaza-, tetraza-, thiaza-, thiadiaza-, thiatriaza-, oxaza-, or oxadiaza-cyclic group, which may bear one or more substituents such as those mentioned below.

Preferred examples of the heterocyclic-thio group comprising the five-membered monocyclic, heterocyclic group include an imidazolylthio group such as 2-imidazolylthio group; a triazolylthio group, either unsubstituted or substituted with a lower alkyl group and/or a phenyl group, for example, 1H-1,2,3-triazol-4-ylthio group, 1-methyl-1H-1,2,3-triazol-4-ylthio group, 1H-1,2,4-triazol-3-ylthio group, 5-methyl-1H-1,2,4-triazol-3-ylthio group, 3-methyl-1-phenyl-1H-1,2,4-triazol-3-ylthio group, 4,5-dimethyl-4H-1,2,4-triazol-3-ylthio group, or 4-carboxymethyl-4H-1,2,4-triazol-3-ylthio or 4-phenyl-4H-1,2,4-triazol-3-ylthio group; an unsubstituted or substituted tetrazolylthio group such as 1H-tetrazol-5-ylthio group, 1-methyl-1H-tetrazol-5-ylthio group, 1-carboxymethyl-1H-tetrazol-5-ylthio group, 1-(2-carboxyethyl)-1H-tetrazol-5-ylthio group, 1-sulfomethyl-1H-tetrazol-5-ylthio group, 1-(2-sulfoethyl)-1H-tetrazol-5-ylthio group, 1-(2-dimethylaminoethyl)-1H-tetrazol-5-ylthio group, 1-phenyl-1H-tetrazol-5-ylthio group or 1-(4-chlorophenyl)-1H-tetrazol-5-ylthio group; a thiazolylthio group or isothiazolylthio group, each either unsubstituted or substituted with a lower alkyl group or a thienyl group, for example, 2-thiazolylthio group, 4-(2-thienyl)-2-thiazolylthio group, 4,5-dimethyl-2-thiazolylthio group, 3-isothiazolylthio group, 4-isothiazolylthio group or 5-isothiazolylthio group; an unsubstituted or substituted thiadiazolylthio group such as 1,2,3-thiadiazol-4-ylthio group, 1,2,3-thiadiazol-5-ylthio group, 1,3,4-thiadiazol-2-ylthio group, 2-methyl-1,3,4-thiadiazol-5-ylthio group, 2-(3-carboxypropionylamino)-1,3,4-thiadiazol-5-ylthio group, 1,2,4-thiadiazol-5-ylthio group, 3-methyl-1,2,4-thiadiazol-5-ylthio group or 1,2,5-thiadiazol-3-ylthio group; a thiatriazolylthio group such as 1,2,3,4-thiatriazol-5-ylthio group; an unsubstituted or substituted oxazolylthio or isoxazolylthio group such as 5-oxazolylthio group, 4-methyl-5-oxazolylthio group, 2-oxazolylthio group, 4,5-diphenyl-2-oxazolylthio group or 3-methyl-5-isooxazolylthio group; an unsubstituted or substituted oxadiazolylthio group such as 1,2,4-oxadiazol-5-ylthio group, 2-methyl-1,3,4-oxadiazol-5-ylthio group, 2-phenyl-1,3,4-oxadiazol-5-ylthio group, 5-(4-nitrophenyl)-1,3,4-oxadiazol-2-ylthio group or 2-(2-thienyl)-1,3,4-oxadiazol-5-ylthio group.

"Unsubstituted or substituted pyridino" group stands for a quaternary ammonium or pyridinium group represented by the formula (III):

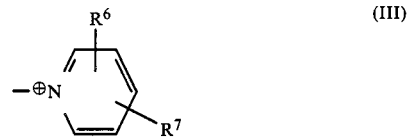

wherein R⁶ and R⁷ are the same or different, and each are a hydrogen atom; a lower (C₁–C₆) alkyl group such as methyl group; a carbamoyl group; a carboxyl group; sulfonic acid residue; or a lower (C₁–C₆) alkoxy group such as methoxy group, or it stands for a quaternary ammonium or pyridinium group represented by the formula (IV)

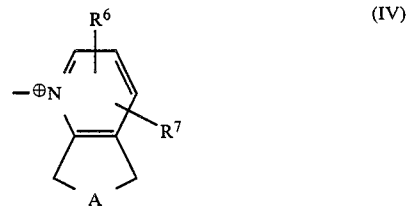

wherein R⁶ and R⁷ are as defined above; and A is —CH₂—, —S—, —O—, or —NH—.

According to a preferred embodiment of this invention, there is provided a new cephalosporin compound of the general formula (Ia)

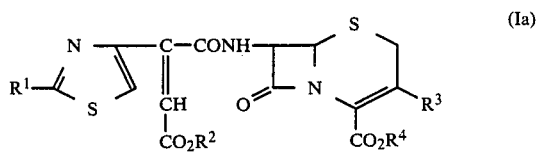

wherein R¹ is an amino group, a tritylamino group, or a trifluoroacetylamino group; R² is a hydrogen atom or a lower alkyl group; R³ is a hydrogen atom, a chloromethyl group, a (1,3,5-thiadiazol-2-yl)thiomethyl group, a (5-methyl-1,3,4-thiadiazol-2-yl)thiomethyl group or a (1-methyl-pyridinium-4-yl)thiomethyl group; and R⁴ is a hydrogen atom, a lower alkyl group, a diphenyl-(C₁–C₄) alkyl group or a lower alkoxymethyl group or a lower alkanoyloxymethyl group such as pivaloyloxymethyl group.

Particular examples of the new compounds of the formula (I) or (Ia) include:

(A) 7-[2-(2-tritylaminothiazol-4-yl)-2-t-butoxycarbonylmethylene-acetamide]-3-(5-methyl-1,3,4-thiadiazol-2-yl)thiomethyl-3-cephem-4-carboxylic acid, its diphenylmethyl ester and its pivaloyloxymethyl ester.

(B) 7-[2-(2-aminothiazol-4-yl)-2-carboxymethyleneacetamido]-3-(5-methyl-1,3,4-thiadiazol-2-yl)thiomethyl-3-cephem-4-carboxylic acid, its trifluoroacetate and its pivaloyloxymethyl ester.

(C) 7-[2-(2-tritylaminothiazol-4-yl)-2-t-butoxycarbonylmethylene-acetamido]-3-chloromethyl-3-cephem-4-carboxylic acid and its diphenylmethyl ester.

(D) 7-[2-(2-tritylaminothiazol-4-yl)-2-t-butoxycarbonylmethyleneacetamido]-3-(1-methylpyridinium-4-yl)thiomethyl-3-cephem-4-carboxylic acid and its diphenylmethyl ester chloride.

(E) 7-[2-(2-aminothiazol-4-yl)-2-carboxymethyleneacetamido]-3-(1-methylpyridinium-4-yl)thiomethyl-3-cephem-4-carboxylic acid, its trifluoroacetate and its diphenylmethyl ester.

The new compound of the formula (I) according to this invention may be prepared by any one of the following methods.

Method 1

In this method, the compound of the formula (V)

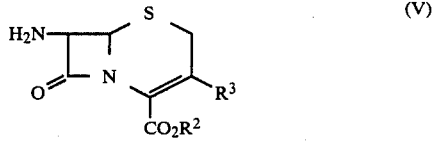
(V)

wherein $R^2$ and $R^3$ are as defined above, or an amino-reactive derivative of the compound of the formula (V) or a salt thereof is reacted with a compound of the formula (VI)

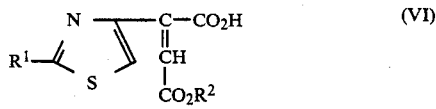
(VI)

wherein $R^1$ and $R^2$ are as defined above, or a carboxyl-reactive derivative of the compound of the formula (VI) or a salt thereof.

Examples of the amino-reactive derivative of the compound (V) include such an imino derivative of Shiffbase type which may be obtained by reaction of the compound (V) with a carbonyl compound such as an aldehyde or ketone, or an enamine-type isomer (tautomer) of said imino derivative; such a sillyl derivative which may be obtained by reaction of the compound (V) with a sillyl compound such as bis-(trimethylsillyl-)acetamide; or such a derivative which may be obtained by reaction of the compound (V) with phosphorus trichloride or phosgene.

Appropriate examples of the salts of the compound (V) or (VI) include an acid-addition salt thereof, for example, a salt of the compound (V) or (VI) with an organic acid such as acetic acid, maleic acid, tartaric acid, benzenesulfonic acid, toluenesulfonic acid; a salt of the compound (V) or (VI) with an inorganic acid such as hydrochloric acid, hydrobromic acid, sulfuric acid, phosphoric acid; a metal salt (carboxylate) of the compound (V) or (VI) with an alkali metal such as sodium and potassium or with an alkaline earth metal such as calcium and magnesium; ammonium salt (carboxylate) of the compound (V) or (VI); an amine salt of the compound (V) or (VI) with an organic amine such as triethylamine and dicyclohexylamine.

Suitable examples of the carboxyl-reactive derivative of the compound (VI) include an acid halide, an acid amide, an acid anhydride, an activated amide and an activated ester of the compound (VI), and especially they may be an acid chloride or an acid bromide of the compound (VI); a mixed acid anhydride of the compound (VI) with an acid, for example, with a substituted phosphoric acid such as dialkylphosphoric acid, phenylphosphoric acid, diphenylphosphoric acid, dibenzylphosphoric acid, a halogenated phosphoric acid, with a dialkyl phosphorous acid, with sulfurous acid, with thiosulfuric acid, with sulfuric acid, with an alkyl carbonate such as methyl carbonate and ethyl carbonate, with an aliphatic carboxylic acid such as pivalic acid, valeric acid, isovaleric acid, 2-ethylacetic acid and trichloroacetic acid, or with an aromatic carboxylic acid such as benzoic acid; an symmetrical acid anhydride of the compound (VI); an activated amide of the compound (IV) formed with imidazole, 4-substituted imidazole, dimethylpyrazole, triazole or tetrazole; an activated ester of the compound (VI) such as cyanomethyl ester, methoxymethyl ester, dimethyliminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenylthio ester, p-cresylthio ester, carboxymethylthio ester, pyranyl ester, pyridyl ester, piperidyl ester or 8-quinolylthio ester; or an ester of the compound (VI) formed with a N-hydroxyl compound such as N,N-dimethylhydroxylamine, 1-hydroxy-2-(1H)-pyridone, N-hydroxysuccinimide, N-hydroxyphthalimide or 1-hydroxy-6-chloro-1H-benzotriazole.

These reactive derivatives of the compound (V) may be properly selected depending on the compound (VI) to be used.

This reaction of the compound (V) with the compound (VI) may usually be conducted in a conventional solvent such as water, acetone, dioxane, acetonitrile, chloroform, methylene chloride, ethylene chloride, tetrahydrofurane, ethyl acetate, N,N-dimethylformamide, pyridine, or in any other solvent which exerts no adverse effect on the progress of this reaction. These solvents may be used as a mixture with water.

In the case where the compound (VI) is used in the form of a free acid or in the form of a salt, the reaction may preferably be conducted in the presence of a condensing agent. Examples of such a condensing agent may be N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; phosphorous acid trialkylester; ethyl polyphosphate; isopropyl polyphosphate; phosphorus oxychloride; phosphorus trichloride; thionyl chloride; oxalyl chloride; triphenylphosphine; 2-ethyl-7-hydroxybenzoisoxazolium salt; 2-ethyl-5-(m-sulfophenyl)isoxazolium hydroxide (intramolecular salt); 1-(p-chlorobenzenesulfonyloxy)-6-chloro-1H-benzotriazole; Willsmeyer reagent as prepared from reaction of dimethylformamide with thionyl chloride, phosgene and phosphorus oxychloride.

This reaction according to Method 1 may also be conducted in the presence of an inorganic or organic base. Examples of these inorganic and organic bases are an alkali metal hydrogen carbonate such as sodium hydrogen carbonate or potassium hydrogen carbonate, an alkali metal carbonate such as sodium carbonate or potassium carbonate, an alkaline earth metal carbonate such as calcium carbonate, a tri-(lower)alkyl amine such as trimethylamine or triethylamine, pyridine, N-(lower-)alkylmorpholine, N,N-di-(lower)alkylbenzylamine.

The reaction as above may be carried out at a non-critical temperature, and may usually be conducted under cooling or under heating.

Method 2

In this method, such compound of the formula (I) in which $R^3$ is the group $-CH_2Y$ is prepared by reacting a compound of the formula (VII)

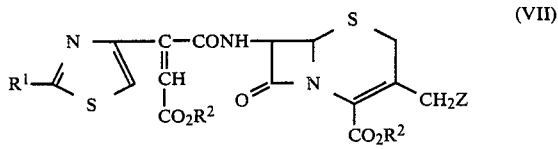
(VII)

where $R^1$ and $R^2$ are as defined above and Z is such a group replaceable by a nucleophilic compound residue, with a nucleophilic compound. For instance, such a class of the compound of the general formula (I) in which $R^3$ denotes a group $-CH_2Y'$ where $Y'$ is an unsubstituted or substituted pyridinio group, or an N-substituted or unsubstituted lower alkylpyridiniothio group, and which is designated as the compound of the formula (I') may be prepared by reaction of the compound (VII) with a pyridine compound of the formula (VIII) or the formula (IX) or a pyridothione compound of the formula (X) shown below, respectively.

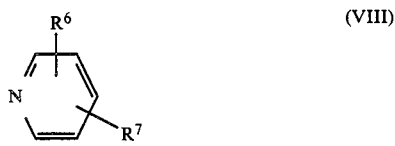
(VIII)

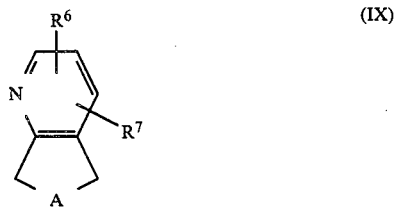
(IX)

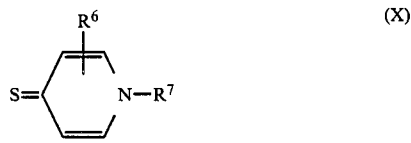
(X)

wherein $R^6$, $R^7$ and A are as defined hereinbefore.

Further, for instance, such another class of the compound of the general formula (I) in which $R^3$ is a group $-CH_2Y$ where Y is a nucleophilic compound residue such as a heterocyclic thio group containing one or more nitrogen atoms in the heterocyclic ring, may be prepared by reaction of the corresponding compound (VII) with a nucleophilic compound such as a nitrogen-containing heterocyclic thiol compound of the formula:

$R^8SH$ where $R^8$ is the nitrogen-containing heterocyclic group as mentioned above.

So far as the above reaction for conversion of the group $-CH_2Z$ at the 3-position of the cephem nucleus of the compound (VII) is limitatively concerned, this reaction is known per se and is substantially the same as those reactions disclosed in many documents of the prior-art and in several patent specifications (see: F. H. Flynn; Cephalosporins and Penicillins, Chapter 4, Vol. 5, p. 151 (1972); Japanese patent publication Nos. 17936/64, 26972/64, 11283/68), and said reaction may be conducted in a manner same as or similar to the reactions of the prior art.

Amongst said nucleophilic compound, the nitrogen-containing heterocyclic thiol compound ($R^8$—SH) may be employed in the form of a free thiol, but it is preferred to be used in the form of its salt (mercaptide) with an alkali metal such as sodium and potassium. This reaction with the thiol may preferably be conducted in a solvent, for example, in an organic solvent which does neither react with water nor with the starting material as used, such as dimethylformamide, dimethylacetoamide, dioxane, acetone, a lower alkanol, acetonitrile, dimethylsulfoxide, and tetrahydrofuran, alone or as mixture thereof. The reaction temperature and reaction time may vary depending upon the kinds of the starting material and the solvent as employed. In general, the reaction temperature may be selected to be in a range of 0° to 100° C., and the reaction time may be chosen to be for several hours to several days. The reaction may be carried out at a neutral pH value or thereabout, usually at a pH value of 2 to 8, preferably of 5 to 8. The reaction may proceed smoothy in the reaction system of a surface-active quaternary ammonium salt such as trimethylbenzylammonium bromide, triethylbenzylammonium bromide and triethylbenzylammonium hydroxide. An advantageous result can be obtained when conducting the reaction under a stream of an unreactive gas such as nitrogen for the purpose of preventing air-oxidation from taking place in the reaction mixture.

The nitrogen-containing heterocyclic thiol compound as the reactant may be prepared, for example, either (i) by a procedure same as or similar to the known methods as disclosed in the "Heterocyclic Chemistry", Chapter 5 (published from John Willey & Sons (1960)); the "Heterocyclic Compounds" Vol. 8, Chapter 1 (published from John Willey & Sons (1967)); the "Advances in Heterocyclic Chemistry" Vol. 9, pages 165–209 (published from Academic Press Co. (1968)) and the "DAI YU-KI KAGAKU" Vol. 15 (edited by Munio Kotake, published from Asakura shoten, Japan) and others, or (ii) by such a method wherein a known heterocyclic thiol or a heterocyclic thiol as obtained in the above-mentioned procedure (i) is subjected to a chemical reaction for converting one or more functional groups, except the thiol group, of said heterocyclic thiol into another ones as desired.

The product compound of the formula (I) according to this invention which have been prepared by any one of the above reactions for the preparation thereof may, if desired, then be subjected to further conventional step(s) for removal of the remaining carboxyl-protecting group and/or the remaining amino-protecting group therefrom, and/or to further conventional step(s) for converting the carboxyl group(s) of the product compound (I) into a metabolically unstable, non-toxic ester (carboxylate) group. The method for removal of the carboxyl-protecting group and/or the amino-protecting group may properly be chosen according to the nature of the protecting groups to be removed.

The amino-protecting group may be removed from the product compound (I) by a conventional deprotecting technique, for example, by hydrolysis or reduction, and for such a product compound bearing an acyl group as the amino-protecting group to be removed, it is feasible to subject such product compound to a reaction with an imino-halogenating agent and then with an imino-etherifing agent, if necessary, followed by hydrolysis. Acid hydrolysis is one of the conventional methods for the removal of the amino-protecting groups and is applicable to the removal of such groups as an alkoxycarbonyl group, formyl group and trityl group. The acids available for this acid hydrolysis may be formic acid, trifluoroacetic acid, p-toluenesulfonic acid, hydrochloric acid and other organic or inorganic acids, and preferably the acids are formic acid, trifluoroacetic acid and hydrochloric acid which afford easy after-treatment of the reaction mixture. These acids for hydrolysis are selected properly according to the nature of the amino-protecting group to be removed. This hydrolysis reaction may be carried out either in the absence of any solvent or in the presence of a solvent such as water, a hydrophilic organic solvent or a mixture of organic solvents. When trifluoroacetic acid is employed for the acid hydrolysis, the reaction may suitably be conducted in the presence of anisole.

The carboxyl-protecting group may be removed also in a conventional manner, for example, by hydrolysis or reduction. Acid hydrolysis is one of the conventional deprotection methods, which is advantageously applicable to the removal of the carboxyl-protecting group of such kind as sillyl group and diphenylmethyl group.

The conversion of the carboxyl group into the metabolically unstable ester group may be performed by a conventional method comprising reacting a metal salt of the corresponding carboxylic acid compound with an alkyl halide such as a pivaloyloxymethyl halide e.g. chloride in a solvent.

The α-(substituted methylene)-α-aminothiazolylacetic acid of the formula (VI) used as the starting material in the aforesaid reactions for the preparation of the new compounds according to this invention may be produced by a synthetic method which has been already reported by the present inventors, and which method comprises reacting aminothiazolylketo acid with a corresponding phosphorane by Witting reaction to produce the reaction product as a mixture of (E)-isomer and (Z)-isomer, and these mixed two isomers may be isolated into single isomer (E) and single isomer (Z).

Examples of the pharmaceutically acceptable salts of the compound of the formula (I) or (Ia) include ordinary non-toxic salts, for example, salts with an alkali metal such as sodium and potassium; salts with an alkaline earth metal such as calcium and magnesium; ammonium salt; salts with an organic base such as trimethylamine, triethylamine, pyridine, picoline, dicyclohexylamine, N,N'-dibenzylethylenediamine; salts with an organic acid such as acetic acid, trifluoroacetic acid, maleic acid, tartaric acid, methanesulfonic acid, benzenesulfonic acid, formic acid and toluenesulfonic acid; salts with an inorganic acid such as hydrochloric acid, hydrobromic acid, sulfuric acid and phosphoric acid; salts with an amino acid such as arginic acid, aspartic acid and glutamic acid.

The compounds of this invention are all novel compounds. Minimum inhibitory concentrations (MIC.) of some of the new compounds against growth of bacteria as determined by agar-dilution method are shown in Table 1 below. As be apparent from Table 1, all the compounds under test of this invention exhibit high antibacterial activity and a wide range of antibacterial spectra, indicating that the new compounds of this invention are useful as antibacterial agent.

TABLE 1

| | MIC (µg/ml) | | |
|---|---|---|---|
| Test microorganism | The compound of Example 2 | The compound of Example 7 | The compound of Example 10 |
| Staphylococcus aureus 209P JC-1 | 3.13 | 0.20 | 0.78 |
| Staphylococcus aureus Smith | 3.13 | 0.39 | 0.78 |
| Escherichia coli NIHJ JC-2 | 0.78 | 0.39 | 12.5 |
| Klebsiella pneumoniae PCI 602 | 0.78 | 0.78 | 25 |
| Proteus mirabillis GN 79 | 0.20 | 1.56 | 50 |
| Proteus vulgaris GN 76 | 0.39 | 3.13 | >50 |
| Proteus rettgeri GN 624 | ≦0.025 | 0.10 | 3.13 |
| Salmonella typhimurium LT-2 | 0.39 | 0.39 | 12.5 |
| Serratia marcescens No. 1 | 0.10 | 0.78 | 25 |
| Pseudomonas aeruginosa MB 3833 | >50 | >50 | >50 |

With regard to the compounds as referred to in Table 1 above, the compound of Example 2 is 7-[2-(2-aminothiazol-4-yl)-2-carboxymethylene-acetamido]-3-(5-methyl-1,3,4-thiadiazol-2-yl)thiomethyl-3-cephem-4-carboxylic acid (Z-isomer) trifluoroacetate, the compound of Example 7 is 7-[2-(2-aminothiazol-4-yl)-2-carboxymethyleneacetamido]-3-(1-methylpyridinium-4-yl)thiomethyl-3-cephem-4-carboxylic acid (Z-isomer) trifluoroacetate, and the compound of Example 10 is 7-[2-(2-aminothiazol-4-yl)-2-carboxymethyleneacetamido]-3-(1-methylpyridinium-4-yl)thiomethyl-3-cephem-4-carboxylic acid (E-isomer) trifluoroacetate.

The new compound of the formula (I) or the formula (Ia) according to this invention, or a pharmaceutically acceptable salt or ester thereof may be formulated into a pharmaceutical composition by mixing with a pharmaceutically acceptable solid or liquid carrier or vehicle when it is to be administered to man for the therapeutic treatment of bacterial infections.

According to a further aspect of this invention, therefore, there is provided a pharmaceutical, antibacterial composition which comprises the compound of the formula (I) or the formula (Ia) as defined hereinbefore or a pharmacuetically acceptable salt or ester thereof as the active ingredient, in combination of a pharmaceutically acceptable carrier for the active ingredient.

The pharmaceutically acceptable carrier as mixed with the active ingredient compound may be an ordinary solid or liquid one, either organic or inorganic, which may be chosen appropriately depending on whether the pharmaceutical formulation as prepared is to be administered orally or non-orally or applied externally. The pharmaceutical composition of this invention may be of any conventional formulation form such as capules, tablets, sugar-coated pills, ointment, suppository, solution, suspension, and emulsion. Other conventional additives, including adjuvant, stabilizing agent, wetting agent, emulsifying agent, buffer solution may also be incorporated into the pharmaceutical composition of this invention containing the compound (I) as the active ingredient.

This invention is now illustrated with reference to the following Reference Examples 1~2 and Examples 1~10. Examples 1~10 illustrate the procedures for preparing the new cephalosporin compounds of this invention, and Reference Examples 1~2 illustrate the procedures for preparing the starting compounds employed for the preparation of the new compounds of this invention.

REFERENCE EXAMPLE 1

Production of 2-t-butoxycarbonylmethylene-2-(2-tritylaminothiazol-4-yl)acetic acid allyester (Z- and E-isomers):

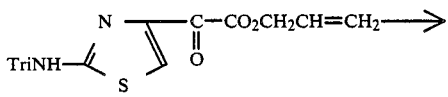

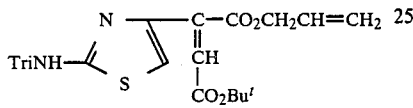

In the formulae above and formulae given later, Tri denotes a trityl group and $Bu^t$ denotes a tert.-butyl group.

2-Oxo-2-(2-tritylaminothiazol-4-yl)acetic acid allylester (900 mg) was dissolved in dimethylformamide (15 ml), to which t-butoxycarbonylmethylenetriphenylphosforan (827 mg) was added. The resultant mixture was stirred for 20 hours at ambient temperature and was concentrated. The concentrate was poured into a solvent mixture of ethyl acetate (100 ml) and water (100 ml) and thus washed with said mixture of ethyl acetate and water. The organic solvent phase was separated out of the resultant mixture, dried over anhydrous magnesium sulfate and then concentrated to dryness under reduced pressure. The solid residue obtained was purified chromatographically on a column of silica gel (Wako-gel C-200) (60 g.). Z and E-isomers of 2-t-butoxycarbonylmethylene-2-(2-tritylaminothiazol-4-yl)acetic acid allyester were thus isolated from each other. Z-isomer was obtained in a yield of 743 mg and showed the following NMR spectra:

NMR (80 MHz, δ value, ppm, CDCl₃): 1.48 (9H, s) 4.80 (2H, bd) 5.15~5.45 (2H, m) 5.70~6.20 (1H, m) 6.40 (1H, s) 6.50 (1H, s) 6.65 (1H, bs) 7.3 (15H, s)

E-isomer was obtained in a yield of 51 mg and showed the following NMR spectra:

NMR (80 MHz, δ value, ppm, CDCl₃): 1.46 (9H, s) 4.70 (2H, bd) 5.2~5.4 (2H, m) 5.7~6.2 (1H, m) 6.50 (1H, bs) 6.75 (1H, s) 6.85 (1H, s) 7.3 (15H, bs)

REFERENCE EXAMPLE 2

Production of 2-t-butoxycarbonylmethylene-2-(2-tritylaminothiazole)acetic acid (Z-isomer)

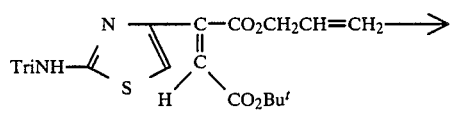

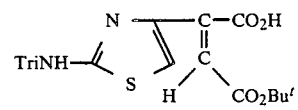

2-t-Butoxycarbonylmethylene-2-(2-tritylaminothiazol-4-yl)acetic acid allylester (Z-isomer) (361 mg) was dissolved in ethyl acetate (10 ml), to which triphenylphosphin (30 mg) and tetrakis-triphenylphosphin palladium (O) (30 mg) were added under ice-cooling. The resultnt mixture was then admixed with a solution of potassium 2-ethylhexanoate (120 mg) in ethyl acetate (5 ml) and stirred for 1 hour at ambient temperature, until crystals were precipitated. To the whole mixture was added isopropylether (50 ml) and the mixture was filtered to recover the precipitate which was then taken into ethyl acetate (30 ml). The resultant solution in ethyl acetate was ice-cooled and adjusted to pH 2.5 by addition of aqueous 5% HCl, followed by washing with water. The solution was dried over anhydrous magnesium sulfate and concentrated under reduced pressure to obtain 2-t-butoxycarbonylmethylene-2-(2-tritylaminothiazolyl-4-yl)acetic acid (Z-isomer) (290 mg).

NMR (80 MHz, δ value, ppm, CDCl₃): 1.41 (9H, s), 6.49 (1H, s), 6.56 (1H, s), 7.3 (16H, bs)

EXAMPLE 1

Production of 7-[2-(2-tritylaminothiazol-4-yl)-2-t-butoxycarbonylmethylene-acetamido]-3-(5-methyl-1,3,4-thiadiazol-2-yl)thiomethyl-3-cephem-4-carboxylic acid diphenylmethylester

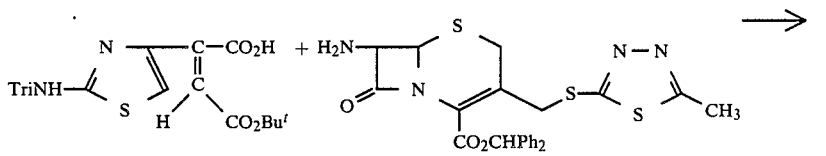

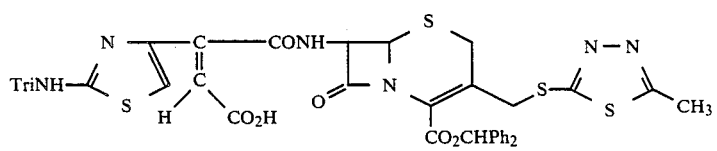

(Ph = Phenyl)

2-t-butoxycarbonylmethylene-2-(2-tritylamino-thiazol-4-yl)acetic acid (Z-isomer) (92 mg) and 7-amino-3-(5-methyl:1,3,4-thiadiazol-2-yl)thiomethyl-3-cephem-4-carboxylic acid diphenylmethylester (204 mg) were dissolved in methylene chloride (5 ml) under a stream of argon gas. The resultant solution was cooled to −30° C. and was admixed with pyridine (0.12 ml). To the solution at −30° C. was further added dropwise phosphorus oxychloride (0.052 ml). The resultant mixture was stirred for 10 minutes at the same temperature (−30° C.), and for 30 minutes at 0° C. The reaction mixture was then poured into a solvent mixture of ethyl acetate (50 ml) and water (30 ml), and thus the organic phase containing the reaction product was washed with water. The organic phase was separated from the aqueous phase, dried over magnesium sulfate and was purified chromatographically on a column of silica gel (Wako gel C-200) developed with a development solvent system comprising toluene-ethyl acetate. The titled compound; 7-[2-(2-tritylaminothiazol-4-yl)-2-t-butoxycarbonylmethyleneacetamido]-3-(5-methyl-1,3,4-thiadiazol-2-yl)thiomethyl-3-cephem-4-carboxylic acid diphenylmethylester (75 mg) was thus obtained.

yl)thiomethyl-3-cephem-4-carboxylic acid diphenylmethylester (Z-isomer) (60 mg) was dissolved in anisole (0.5 ml), and the resultant solution was ice-cooled. The cooled solution was admixed with trifluoroacetate acid (2 ml), and the admixture obtained was stirred for 4 hours at 0° to 5° C. The resulting reaction solution was poured into isopropylether (50 ml), to precipitate the titled compound. The precipitate was removed by filtration to give 7-[2-(2-aminothiazol-4-yl)-2-carboxymethylene-acetamido]-3-(5-methyl-1,3,4-thiadiazol-2-yl)thiomethyl-3-cephem-4-carboxylic acid (Z-isomer) trifluoroacetate (20 mg) as powder.

NMR (90 MHz, δ value, ppm, DMSO-$d_6$): 2.66 (3H, s), 3.50, 3.80 (2H, ABq, J=18 Hz), 4.15, 4.56 (2H, ABq, J=14.4), 5.14 (1H, d, J=5.4 Hz), 5.72 (1H, d.d, J=5.4 Hz, J=8.0 Hz), 6.30 (1H, s), 6.63 (1H, s). 9.28 (1H, d, J=8.0 Hz)

EXAMPLE 3

Production of 7-[2-(2-tritylaminothiazol-4-yl)-2-t-butoxycarbonylmethylene-acetamido]-3-(5-methyl-1,3,4-thiadiazol-2-yl)thiomethyl-3-cephem-4-carboxylic acid pivaloyloxymethylester (Z-isomer)

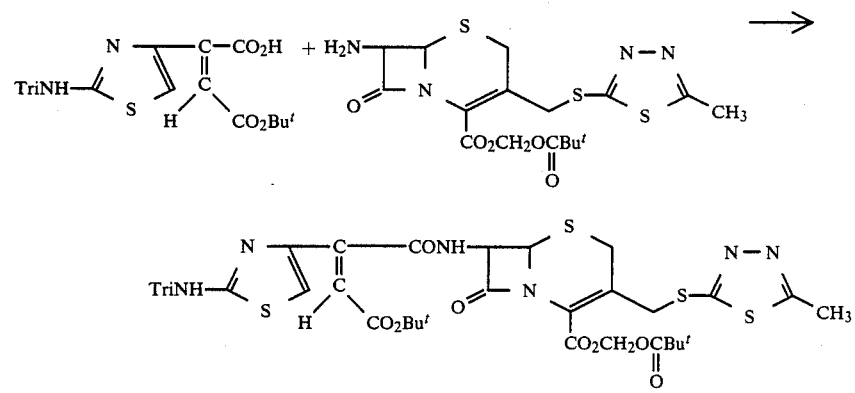

NMR (90 MHz, δ value, ppm, CDCl$_3$): 1.57 (9H, s), 2.77 (3H, s), 3.72 (2H, bs), 4.25, 4.60 (2H, ABq, J=15.3 Hz), 5.12 (1H, d, J=6.0 Hz), 6.08 (1H, d, d, J=6.0 Hz, J=8.2 Hz), 6.60 (1H, d, J=8.2 Hz), 6.62 (1H, s), 6.72 (1H, s), 7.02 (1H, s), 7.40 (16H, m)

EXAMPLE 2

Production of 7-[2-(2-aminothiazol-4-yl)-2-carboxymethylene-acetamido]-3-(5-methyl-1,3,4-thiadiazol-2-yl)thiomethyl-3-cephem-4-carboxylic acid (Z-isomer) trifluoroacetate 7-amino-3-(5-methyl-1,3,4-thiadiazol-2-yl)thiomethyl-3-cephem-4-carboxylic acid pivaloyloxymethylester as the starting material was processed in the same manner as in Example 1, to obtain the titled compound: 7-[2-(2-tritylaminothiazol-4-yl)-2-t-butoxycarbonylmethyleneacetamido]-3-(5-methyl-1,3,4-thiadiazol-2-yl)thiomethyl-3-cephem-4-carboxylic acid pivaloyloxymethylester (Z-isomer).

NMR (90 MHz, δ value, ppm, CDCl$_3$): 1.20 (9H, s), 1.50 (9H, s), 2.72 (3H, s), 3.70 (2H, bs), 4.15, 4.64 (2H, ABq, J=14.5 Hz), 5.05 (1H, d, J=5.4 Hz), 5.90 (3H, m),

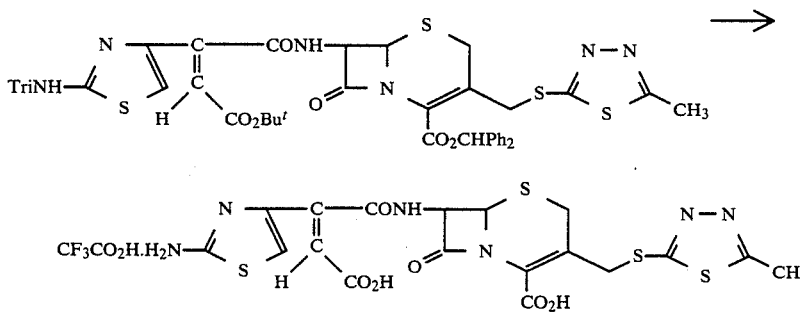

7-[2-(2-tritylaminothiazol-4-yl)-2-t-butoxycarbonylmethylene-acetamido]-3-(5-methyl-1,3,4-thiadiazol-2-

6.58 (1H, s), 5.62 (1H, s), 7.30 (15H, s)

EXAMPLE 4

Production of 7-[2-(2-aminothiazol-4-yl)-2-carboxymethylene-acetamido]-3-(5-methyl-1,3,4-thiadiazol-2-yl)thiomethyl-3-cephem-4-carboxylic acid pivaloyloxymethylester (Z-isomer)

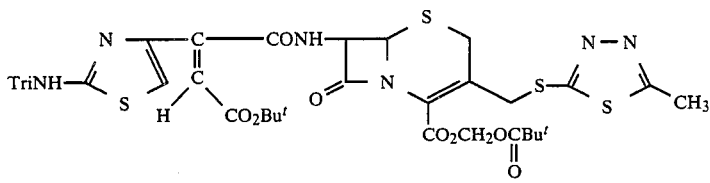

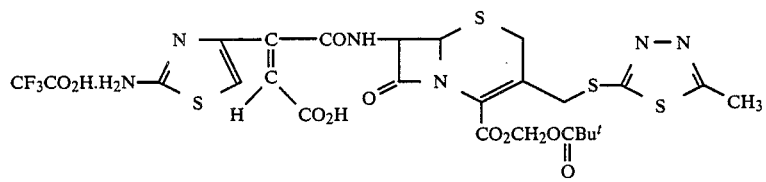

7-[2-(2-tritylaminothiazol-4-yl)-2-t-butoxycarbonylmethylene-acetamido]-3-(5-methyl-1,3,4-thiadiazol-2-yl)thiomethyl-3-cephem-4-carboxylic acid pivaloyloxymethylester (Z-isomer) (30 mg) as the starting material was processed in the same manner as in Example 2, to obtain the titled compound: 7-[2-(2-aminothiazol-4-yl)-2-carboxymethyleneacetamido]-3-(5-methyl-1,3,4-thiadiazol-2-yl)thiomethyl-3-cephem-4-carboxylic acid pivaloyloxymethylester (Z-isomer) trifluoroacetate (5 mg).

IR(Nujol): 1980 cm$^{-1}$

NMR (90 MHz, δ value, ppm, DMSO-d$_6$): 1.05 (9H, s), 2.60 (3H, s), 3.62 1 (2H, bs), 4.05, 4.45 (2H, ABq, J=15.3 Hz), 5.10 (1H, d, J=6.0 Hz), 5.62~5.87 (3H, m), 6.22 (1H, s), 6.55 (1H, s), 9.20 (1H, d, J=9.2 Hz)

EXAMPLE 5

Production of 7-[2-(2-tritylaminothiazol-4-yl)-2-t-butoxycarbonylmethylene-acetamido]-3-chloromethyl-3-cephem-4-carboxylic acid diphenylmethylester (Z-isomer)

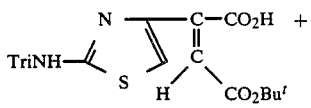 +

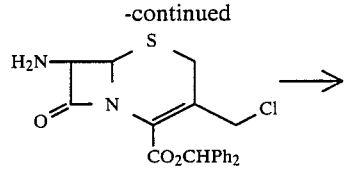

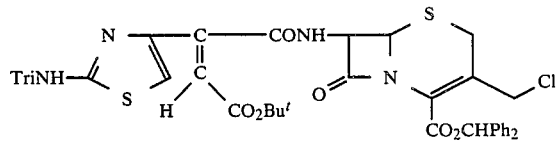

7-amino-3-chloromethyl-3-cephem-4-carboxylic acid diphenylmethylester as the starting material was processed in the same manner as in Example 1, to obtain the titled compound: 7-[2-(2-tritylaminothiazol-4-yl)-2-t-butoxycarbonylmethylene-acetamido]-3-chloromethyl-3-cephem-4-carboxylic acid diphenylmethyl ester (Z-isomer).

NMR (90 MHz, δ value, ppm, CDCl$_3$): 1.48 (9H, s), 3.40, 3.72 (2H, ABq, J=18 Hz), 4.35 (2H, s), 5.08 (1H, d, J=5.4 Hz), 6.00 (1H, d.d, J=5.4 Hz, J=8.2 Hz), 6.50 (1H, s), 6.62 (1H, s), 6.95 (1H, s), 7.30 (16H, m)

EXAMPLE 6

Production of 7-[2-(2-tritylaminothiazol-4-yl)-2-t-butoxycarbonylmethylene-acetamido]-3-(1-methylpyridinium-4-yl)thiomethyl-3-cephem-4-carboxylic acid diphenylmethylester-chloride (Z-isomer)

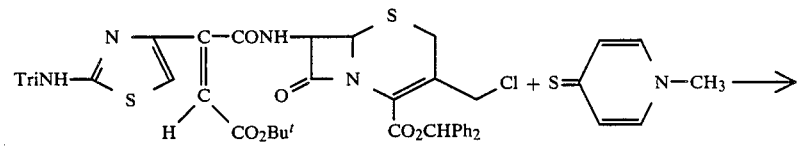

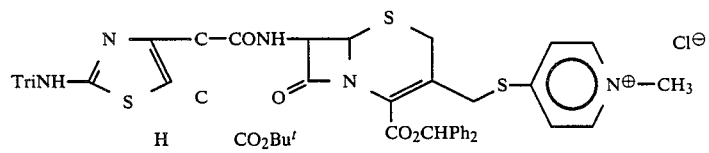

7-[2-(2-tritylaminothiazol-4-yl)-2-t-butoxycarbonylmethylene-acetamido]-3-chloromethyl-3-cephem-4-carboxylic acid diphenylmethylester (Z-isomer) (60 mg)

was dissolved in dry tetrahydrofurane (5 ml), to which N-methylpyridothione

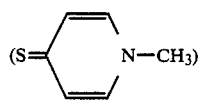

(15 mg) was added. The resulting mixture was stirred for 5 hours at ambient temperature. The reaction solution was poured into ethyl ether (50 ml), to precipitate to solid comprising the titled compound. This solid was removed by filtration and washed with ethyl ether. The titled compound (51 mg) was thus obtained.

NMR (90 MHz, δ value, ppm, CDCl$_3$): 1.45 (9H, s), 3.68 (2H, bs), 4.30 (5H, bs), 5.05 (1H, d, J=4.8 Hz), 5.90 (1H, d.d, J=4.8 Hz, J=8.2 Hz), 6.45 (1H, s), 6.58 (1H, s), 6.85 (1H, s), 7.30 (16H, m), 7.65, 8.72 (4H, A$_2$B$_2$q, J=6.4 Hz)

EXAMPLE 7

Production of 7-[2-(2-aminothiazol-4-yl)-2-carboxymethylene-acetamido]-3-(1-methylpyridinium-4-yl)thiomethyl-3-cephem-4-carboxylic acid trifluoroacetate (Z-isomer)

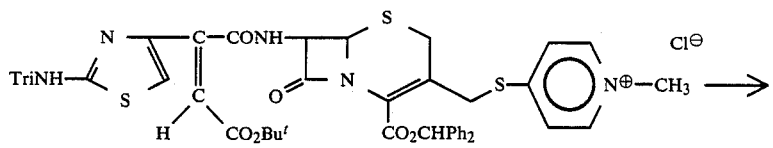

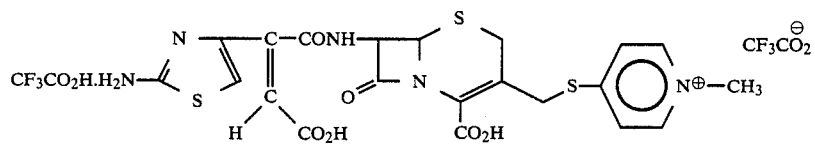

7-[2-(2-tritylaminothiazol-4-yl)-2-t-butoxycarbonylmethylene-acetamido]-3-(1-methylpyridinium-4-yl)thiomethyl-3-cephem-4-carboxylic acid diphenylmethylester chloride (Z-isomer) (70 mg) was dissolved in anisole (0.5 ml) and the solution obtained was ice-cooled. The cooled solution was admixed with trifluoroacetic acid (5 ml) and stirred for 4 hours at 0° to 5° C. The reaction solution was poured into isopropyl ether (50 ml), to precipitate the tilted compound trifluoroacetate. The precipitate was removed by filtration and washed with dry tetrahydrofuran, to obtain the titled compound trifluoroacetate (32 mg)

NMR (90 MHz, δ value, ppm, DMSO-d$_6$): 3.40, 3.75 (2H, ABq, J=17.1 Hz), 4.12 (3H, s), 4.38 (2H, s), 5.15 (1H, d, J=5.4 Hz), 5.72 (1H, d.d, J=5.4 Hz, J=8.1 Hz), 6.30 (1H, s), 5.60 (1H, s), 7.95, 8.65 (4H, A$_2$B$_2$q, J=7.2 Hz), 9.28 (1H, J=8.1 Hz)

EXAMPLE 8

Production of 7-[2-(2-tritylaminothiazol-4-yl)-2-t-butoxycarbonylmethylene-acetamido]-3-chloromethyl-3-cephem-4-carboxylic acid diphenylmethylester (E-isomer)

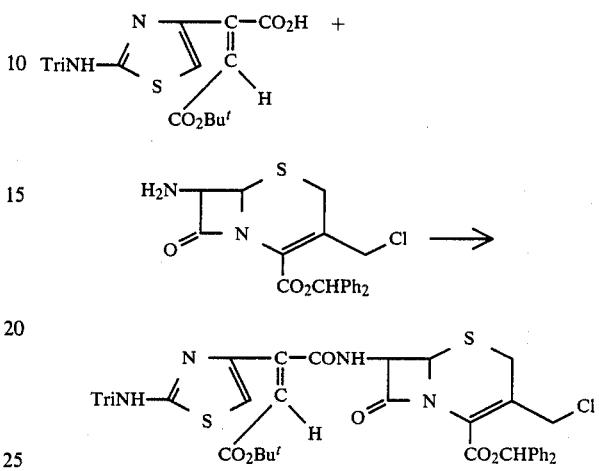

2-t-butoxycarbonylmethylene-3-(2-tritylaminothiazol-4-yl)acetic acid (E-isomer) as the starting material and 7-amino-3-chloromethyl-3-cephem-4-carboxylic acid diphenylmethylester were reacted with each other and the reaction product was processed in the same manner as in Example 1, to yield the titled compound (E-isomer).

NMR (90 MHz, δ value, ppm, CDCl$_3$): 1.40 (9H, s), 3.25, 3.65 (2H, ABq, J=17.1 Hz), 4.40 (2H, s), 5.06 (1H, d, J=5.4 Hz), 6.00 (1H, d.d, J=5.4 Hz, J=9 Hz), 6.61 (1H, s), 6.70 (1H, bs), 6.92 (1H, s), 6.98 (1H, s), 7.3 (15H, bs), 9.22 (1H, d, J=9 Hz)

EXAMPLE 9

Production of 7-[2-(2-aminothiazol-4-yl)-2-carboxymethylene-acetamido]-3-(1-methylpyridinium-4-yl)thiomethyl-3-cephem-4-carboxylic acid diphenylmethylester chloride (E-isomer)

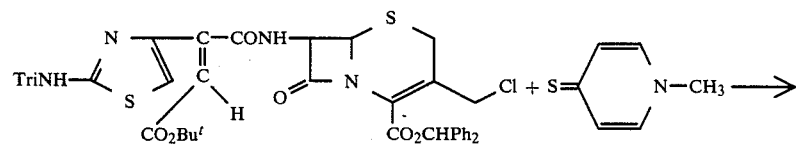

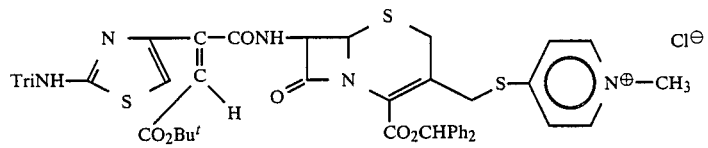

7-[2-(2-tritylaminothiazol-4-yl)-2-t-butoxycarbonyl-methylene-acetamido]-3-chloromethyl-3-cephem-4-carboxylic acid diphenylmethylester (E-isomer) and N-methylpyridothione were reacted with each other and the reaction product was processed in the same manner as in Example 6, to afford the titled compound (E-isomer).

NMR (90 MHz, δ value, ppm, CDCl₃): 1.35 (9H, s), 3.28, 3.72 (2H, ABq, J=18 Hz), 4.35 (5H, bs), 5.03 (1H, d, J=5.9 Hz), 5.82 (1H, d.d, J=5.9 Hz, J=9 Hz), 6.55 (1H, s), 6.72 (1H, bs), 6.85 (1H, s), 6.88 (1H, s), 7.3 (15H, bs), 7.58, 8.70 (4H, A₂B₂q, J=6.3 H), 9.20 (1H, d, J=9 Hz)

EXAMPLE 10

Production of 7-[2-(2-aminothiazol-4-yl)-2-carboxymethylene-acetamido]-3-(1-methylpyridinium-4-yl)thiomethyl-3-cephem-4-carboxylic acid trifluoroacetate (E-isomer)

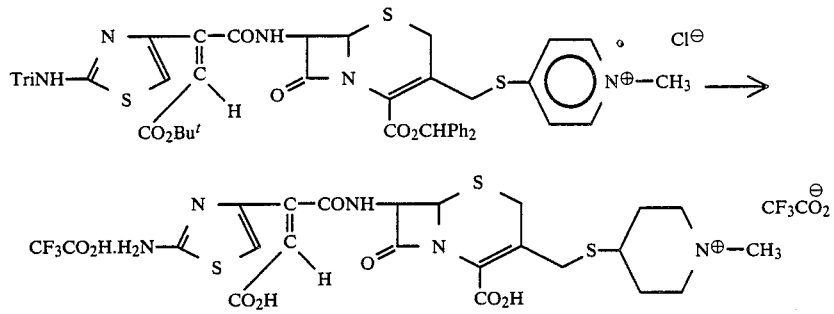

7-[2-(2-tritylaminothiazol-4-yl)-2-t-butoxycarbonyl-methylene-acetamido]-3-(1-methylpyridinium-4-yl)thiomethyl-3-cephem-4-carboxylic acid diphenylmethylester chloride (E-isomer) were reacted with each other and the reaction product was processed in the same manner as in Example 7, to give the titled compound (E-isomer).

NMR (90 MHz, δ value, ppm, DMSO-d₆): 3.45, 3.80 (2H, ABq, J=16.2 Hz), 4.18 (3H, s), 4.40 (2H, s), 5.25 (1H, d, J=5.9 Hz), 5.70 (1H, d.d, J=5.9 Hz, J-8.1 Hz), 5.95 (1H, s), 6.92 (1H, s), 8.00, 8.70 (4H, A₂B₂q, J=6.3 Hz), 9.60 (1H, d, J=8.1 Hz)

What we claim is:
1. 7-[2-(2-aminothiazol-4-yl)-2-carboxymethyleneacetamido]-3-(5-methyl-1,3,4-thiadiazol-2-yl)thiomethyl-3-cephem-4-carboxylic acid (Z-isomer), its trifluoroacetate and its sodium salt.

* * * * *